United States Patent
Raza et al.

(10) Patent No.: US 10,751,212 B2
(45) Date of Patent: Aug. 25, 2020

(54) MULTILAYER DRESSING DEVICE AND METHOD FOR PREVENTING AND TREATING PRESSURE ULCERS AND CHRONIC WOUNDS

(71) Applicants: Maryam Raza, Dallas, TX (US); Ahmed Masud Choudri, Dallas, TX (US)

(72) Inventors: Maryam Raza, Dallas, TX (US); Ahmed Masud Choudri, Dallas, TX (US)

(*) Notice: Subject to any disclaimer, the term of this patent is extended or adjusted under 35 U.S.C. 154(b) by 0 days.

(21) Appl. No.: 15/731,541

(22) Filed: Jun. 26, 2017

(65) Prior Publication Data

US 2018/0369009 A1 Dec. 27, 2018

(51) Int. Cl.
*A61F 5/30* (2006.01)
*A61F 13/02* (2006.01)
(Continued)

(52) U.S. Cl.
CPC .......... *A61F 5/30* (2013.01); *A61F 13/00029* (2013.01); *A61F 13/00038* (2013.01); *A61F 13/025* (2013.01); *A61F 13/0206* (2013.01); *A61F 13/0213* (2013.01); *A61F 13/069* (2013.01); *A61L 15/225* (2013.01); *A61L 15/24* (2013.01); *A61L 15/26* (2013.01); *A61L 15/425* (2013.01); *A61L 15/44* (2013.01); *A61L 15/58* (2013.01); *A61L 15/60* (2013.01);
(Continued)

(58) Field of Classification Search
CPC ............ A61M 1/0088; A61F 13/00051; A61F 2013/00089; A61F 2013/00638; A61F 13/069; A61F 2013/00404; A61F 2013/51492; A61F 2013/15024
See application file for complete search history.

(56) References Cited

U.S. PATENT DOCUMENTS

| | | | | |
|---|---|---|---|---|
| 4,064,565 A | * | 12/1977 | Griffiths | A42B 3/121 2/412 |
| 4,673,605 A | * | 6/1987 | Sias | A61G 7/05707 428/120 |

(Continued)

*Primary Examiner* — Adam Marcetich

(57) ABSTRACT

The present invention provides a device and method for preventing or curing pressure ulcers or chronic wounds. A multilayer dressing comprises a soft silicone jell layer of a suitable thickness which is placed in the multilayer dressing, above an absorbent layer. The matrix of the silicone jell layer is populated with a plurality of silicone beads of suitable size. The beads are connected to each other, and to the silicone jell layer. Breathing of wound and substantial supply of oxygen to the wound is duly insured for all layers of the multiple layer dressing. The beads play a pivotal role in promoting the effectiveness and performance of the multilayer dressing by acting as the plurality of effective cushions, as they absorb and uniformly redistribute a patient's body weight across the entire applied dressing area. The low adhering adhesive coating of about 5 mm in width is applied to the peripheral edges of all the layers. Unlike the multilayer dressing already available in the market, skipping the application of low adhering adhesive coatings on the entire top and bottom surfaces of the layers helps in promoting overall breathability and consequently, the efficiency of the multilayer dressing of the present invention.

6 Claims, 3 Drawing Sheets

(51) Int. Cl.
*A61L 15/22* (2006.01)
*A61L 15/42* (2006.01)
*A61L 15/44* (2006.01)
*A61L 15/58* (2006.01)
*A61L 15/60* (2006.01)
*A61F 13/00* (2006.01)
*A61F 13/06* (2006.01)
*A61L 15/26* (2006.01)
*A61L 15/24* (2006.01)

(52) U.S. Cl.
CPC ........... *A61F 2013/00272* (2013.01); *A61F 2013/00404* (2013.01)

(56) References Cited

U.S. PATENT DOCUMENTS

| | | | | |
|---|---|---|---|---|
| 4,962,769 A * | 10/1990 | Garcia | ........... | A61F 13/535 128/889 |
| 5,105,490 A * | 4/1992 | Shek | ........... | A47C 27/00 5/693 |
| 5,251,414 A * | 10/1993 | Duke | ........... | B32B 5/26 52/309.16 |
| 5,618,263 A * | 4/1997 | Alivizatos | ........... | A61F 5/05841 128/878 |
| 5,733,012 A * | 3/1998 | Jones | ........... | A47C 3/16 297/284.1 |
| 6,022,610 A * | 2/2000 | Phan | ........... | A61F 13/5323 428/171 |
| 2003/0211248 A1* | 11/2003 | Ko | ........... | A61F 13/15658 427/385.5 |
| 2004/0018227 A1* | 1/2004 | Park | ........... | A61F 13/00991 424/445 |
| 2005/0137514 A1* | 6/2005 | Vito | ........... | B32B 5/024 602/75 |
| 2007/0163048 A1* | 7/2007 | Kimball | ........... | A47C 20/021 5/632 |
| 2007/0185463 A1* | 8/2007 | Mulligan | ........... | C03C 12/00 604/305 |
| 2007/0277282 A1* | 12/2007 | Sheppell | ........... | A41D 13/1236 2/69 |
| 2009/0227969 A1* | 9/2009 | Jaeb | ........... | A61M 1/0088 604/313 |
| 2009/0246449 A1* | 10/2009 | Jusiak | ........... | A47C 27/085 428/99 |
| 2010/0160874 A1* | 6/2010 | Robinson | ........... | A61M 1/0023 604/313 |
| 2011/0034906 A1* | 2/2011 | Malhi | ........... | A61M 1/0088 604/543 |
| 2012/0016323 A1* | 1/2012 | Robinson | ........... | A61F 13/0216 604/319 |
| 2013/0150815 A1* | 6/2013 | Luckemeyer | ........... | A61F 13/00068 604/319 |
| 2013/0165836 A1* | 6/2013 | Locke | ........... | A61L 15/42 602/44 |
| 2014/0082840 A1* | 3/2014 | Khowaylo | ........... | A47G 9/0246 5/499 |
| 2014/0249495 A1* | 9/2014 | Mumby | ........... | A61F 13/00059 604/359 |
| 2015/0094672 A1* | 4/2015 | Blucher | ........... | A61L 15/42 604/304 |
| 2015/0141941 A1* | 5/2015 | Allen | ........... | A61M 1/0088 604/319 |
| 2015/0182677 A1* | 7/2015 | Collinson | ........... | A61F 13/0206 604/319 |
| 2017/0189236 A1* | 7/2017 | Locke | ........... | A61F 13/00068 |
| 2017/0217119 A1* | 8/2017 | Lee | ........... | B32B 3/12 |
| 2017/0312406 A1* | 11/2017 | Svensby | ........... | A61F 13/00068 |

* cited by examiner

MULTILAYER DRESSING DEVICE AND METHOD FOR PREVENTING AND TREATING PRESSURE ULCERS AND CHRONIC WOUNDS

CROSS-REFERENCE TO RELATED APPLICATIONS

Not applicable

FEDERALLY SPONSORED RESEARCH OR DEVELOPMENT

Not applicable

REFERENCE TO SEQUENCE LISTING, A TABLE, OR A COMPUTER LISTING APPENDIX

Not applicable

COPYRIGHT NOTICE

A portion of the disclosure of this patent document includes material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the present invention generally, relate to a multilayer dressing for the prevention and treatment of pressure ulcers and chronic wounds. In particular, the present invention relates to a multilayer dressing comprising pressure absorbing and pressure redistribution capability, and method for making the dressing.

BACKGROUND OF THE INVENTION

Pressure ulcers also referred as pressure sores are common in patients who are bedridden for a fairly long period and/or may be wheelchair bound. The onset of pressure ulcers can increase hospital stays by as much as 50% or more. For those residing in nursing homes, pressure sores can complicate what should be a restful experience to a punishing stay. For those required to use a wheelchair to get around, pressure ulcers may cause extra inconvenience already being suffered by a patient. All pressure ulcer sufferers are at an increased risk of infection. Pressure ulcers may even lead to sepsis and/or to early death.

Pressure ulcers lesions may start off about one half inch wide and become as large as the size of a palm of a hand or even larger. Surface size is only one measure of the extent of a pressure sore. A pressure sore typically starts at the surface of the skin. If left untreated even for a short time, a pressure sore may extend deep into muscle and/or bone.

Pressure ulcers may be classified into the following stages: Stage 1, a lesion of the epidermis (outer surface of the skin) which is reddish in color on lighter-skinned people and purplish or bluish on dark skinned people. Stage 2 may be a superficial damage to the epidermis with a blister or an abrasion. Stage 3, may be a lesion that extends to subcutaneous tissue, and stage 4 is a lesion that may extend to muscle or bone.

People with reduced ability to move are most susceptible to pressure ulcers. It is believed that pressure ulcers are the result of continuous pressure and/or friction at a particular area of skin, particularly close to bone or cartilage, such as the spine, knees, ankles, heels, back, hips, and coccyx (tailbone).

A number of factors influence the initiation and propagation of pressure ulcers directly or indirectly. For example, the factors may include but are not limited to, pressure, friction, shear, etc. . . . the role of some of the most pertinent factors is as following:

Pressure:

People with reduced ability to move are the most susceptible to pressure ulcers. It is believed that pressure ulcers are the result of continuous pressure and/or friction at a particular area of skin, particularly an area of skin close to bone or cartilage, such as the spine, knees, ankles, heels, back, hips, and coccyx (tailbone).

Estimates are that more than one million people suffer from pressure sores America alone. The numbers of people who will be at risk of suffering from pressure ulcers are likely to increase dramatically because (i) older people are more likely to be involuntarily immobile, (ii) the skin of people tends to thin as they age, and (iii) a large cohort of people are about to start leaving middle age.

Shear

Shearing action occludes blood flow more easily than compression. For example, it is easier to cut off flow in a water hose by bending rather than by pinching it. So it is safe to assume that shear is more significant than normal pressure in promoting pressure ulcers. Areas of the body particularly susceptible to shearing action include ischia tuberosities, heels, shoulder blades and elbows. These are areas of the body are frequently supported when in a position (such as sitting or lying semi-recumbent) which allows forward slide. Superficial pressure ulcers caused by shearing action tend to have uneven appearance.

Friction

Friction, along with normal pressure and shear is also considered to be a cause of pressure ulcers. Friction can cause pressure ulcers both directly and indirectly. In the indirect sense, friction is necessary to generate shearing forces and the skin weakened by pressure ischemia may be more susceptible to friction and the both pressure and shear act together to a relatively quick skin breakdown. Reduced friction prevents further skin breakdown, and helps reduce the risk that an affected area could be further contaminated by the bowel and/or urinary incontinence suffered by some patients. However, healing still is uncertain and may take weeks or even months.

Immobility

Immobility is not a primary cause of pressure ulcers, but in the presence of additional factors it can initiate pressure ulcers. Patients with profound immobility but intact sensation rarely develop pressure ulcers. Conversely, comatose patients, even with intact sensation, can develop pressure ulcer, as they cannot communicate regarding pain of increased pressure threshold. The pain of tissue ischemia ensures that these patients frequently ask for their position to be changed. Patients with orthopedic casts should be encouraged to report any discomfort and pain in order to prevent iatrogenic pressure ulcers.

Failure of Reactive Hyperamia Cycle:

It is a well-known fact that tissue distortion causes ischemia that in turn stimulates protective movements to relieve pressure and circulatory activity to restore normal blood flow in the affected areas. These protective movements are often reflexes as the person is unaware of making them. However, if these prompt actions prove insufficient to relieve ischemia, the central nervous system is stimulated by constant signals of discomfort and pain to make sure that the pressure is relieved before any permanent damage occurs. Once the pressure is relieved, and the circulation restored, local capillaries begin to dilate and increased blood flow takes place, referred to as reactive hyperemia. As a result, a bright pink transitory patch appears on the skin, often called blanching erythema because it blanches on pressure unlike the dull red non-blanching erythema that indicates tissue damage reactive hyperemia ensures a rapid restoration of oxygen and carbon dioxide balance; it also flushes out waste products. Erythema subsides as soon as tissues are restored to their resting state.

The basic measure for treatment and/or prevention of pressure ulcers requires frequent turning by a caregiver of an immobile patient. To some extent, a wheelchair bound person may be able to move the potentially affected portions of his own body by himself. Turning is recommended at least once every two hours. Each time the body is turned, pressure is at least temporarily relieved from the areas previously under pressure and allows them to be air-cooled. However, this cannot qualify as the prevention or treatment of pressure ulcers.

Other measures for preventing and/or treating pressure ulcers may include, having the patient rest on an alternating pressure mattress and/or on an air mattress having an air-permeable surface. The purpose of such mattresses is to temporarily transfer pressure from the pressure ulcer to the nearby parts of the body and to provide airflow to the pressure ulcers, which among other things, could allow for cooling of the affected tissue. Even when mattresses are efficacious, they are expensive to buy and expensive to operate and maintain.

To prevent or alleviate pressure ulcers, various types of cushions and pads have been designed. As some are disclosed in the prior art, for example: U.S. Pat. No. 3,721,232 discloses "a method for treating and/or preventing pressure sores. The method comprises the steps of: applying a cushion in indirect or direct contact with substantially the entire surface of a pressure sore area. The cushion is preferably circular in shape with a diameter between about 1.5 and about 6 times its height. In the preferred embodiment, the cushion has a silicone elastomeric shell, with the portion of the shell intended to be in occlusive contact with the pressure sore having a smooth outer surface. In the preferred embodiment, the cushion is partially filled, and the filling material is silicone gel. The cushion may be held in place by means of a strap, wrap, bandage or similar device." Some pads are made of foam or gel, and some are filled with air or water. These cushions or pads have a body-contacting surface area which is intended to distribute the pressure from lying on a bed. Some of these pads and cushions are formed with a void, with the pressure ulcers to be positioned over the void. Some of the voids are formed by having the pad or cushion shaped as a donut or ring."

Another prior art, U.S. Pat. No. 7,982,087 titled: "A wound dressing" discloses a transparent upper layer, an absorbent layer comprising a plurality of apertures arranged in a lattice pattern, and a low adherent wound contact layer provided with a plurality of apertures arranged in a lattice pattern such the apertures of this layer are congruent with the apertures of the absorbent layer.

Another prior art, U.S. Pat. No. 7,141,032 titled: An Apparatus and methods for preventing and/or healing pressure ulcers, discloses "Protective devices to protect a plurality of body parts having a bony portion with a soft tissue layer between the bony portion and an outer skin layer, have an inner surface which conforms to the body part to be protected and are applied to the body part to reduce pressure exhibited at the interface between the bony portion and the soft tissue layer, across the soft tissue and outer skin layers and at the interface between the outer skin layer and a support surface. The protective devices may be made of any material suitable for distributing the weight of the body part over an extended area and volume and may include a mushy material, a hard shell, a hydro absorptive material, and a wound dressing with medication. The body part to be protected includes at least one of the heel, trochanter, knee, sacrum, coccyx, ischium, scapula, elbow, ankle, buttocks and occiput: The protective devices may be secured to the body part directly or via a garment or any other suitable securing means."

Another prior art, U.S. Pat. No. 5,340,363 titled: Wound Dressing, discloses "a porous hydrophobic, layer adapted to directly contact the wound during use and an adjacent absorbent layer attached to said hydrophobic layer, said hydrophobic layer comprising an elastic net-like porous reinforcing component substantially encapsulated by a soft and elastic hydrophobic gel while retaining the porosity of said reinforcing component, said hydrophobic layer thus including openings which permit wound exudate to pass through said hydrophobic layer to be absorbed by said outer absorbent layer."

Another prior art, U.S. Pat. No. 5,579,570 titled: Multi-layer dressing, comprising a molecular filtration membrane having a maximum pore size in the range of from 0.001 µm to 0.5 µm, and preferably in the range of from 0.01 µm to 0.25 µm. The wound dressings may also comprise an absorbent layer atop the molecular filtration membrane and/or a wound contact layer of wound-friendly bio-absorbable material for contacting the wound. In use, the molecular filtration membrane retains high molecular weight biopolymers and wound healing factors at the wound surface while excluding bacteria and allowing rapid egress of wound exudate through the membrane into the absorbent layer. Wound dressing for use, with exuding wounds, comprising a porous hydrophobic layer adapted to directly contact the wound during use and an adjacent absorbent layer attached to said hydrophobic layer, said hydrophobic layer comprising of an elastic net-like porous reinforcing component substantially completely encapsulated by a soft and elastic hydrophobic gel while retaining the porosity of said reinforcing component, said hydrophobic layer thus including openings which permit wound exudate to pass through said hydrophobic layer to be absorbed by said outer absorbent layer."

Treatment of pressure ulcers usually requires weeks or months for a successful resolution. Unlike the present invention, the efficacy of the cushions and the pads used in the disclosed above referenced prior art still leaves much to be desired. For example, none of the prior art disclosed above, addresses how to mitigate the effects of normal pressure, or precisely, the distribution of body weight (static and dynamic) of the patient's body part. All other pressure ulcers causing or contributing factors, for example, including but not limited to friction, shear, immobility, or excessive movements of the patient in the bed are sub-set of normal pressure, which is the body weight of the patient (static and dynamic). The soft silicone jell pad, which is an integral part of the multilayer dressing of the present invention, absorbs and uniformly distributes the pressure to other body parts of the patient over an extended surface area, and finally the pressure or body weight of the patient is transferred to the patient's bed and dissipates. The multilayer dressing of the present invention addresses the prevention and treatment of pressure ulcers or chronic wounds more efficiently/effectively than any other prior art disclosed above.

SUMMARY OF THE INVENTION

In achieving the forgoing and other objectives in accordance with the purpose of the present invention, a dressing is devised for the prevention and treatment of pressure ulcers. The designing of the multilayer dressing of the present invention, takes into consideration and understanding of the role of various factors such as, body weight (pressure) of the patient, estimation of friction, shear and other contributing factors in causing the pressure ulcers.

It is to be understood that the present invention is not limited to the particular methodology, system, techniques, uses, and applications, described herein, as these may vary. It is also to be understood that the terminology used herein is for the purpose of describing particular embodiments only, and is not intended to limit the scope of the present invention in any manner or fashion.

In one embodiment of the present invention, a method for an exemplary sequence of the mode of action for devising the multilayer pressure ulcer dressing includes a silicone jell pad of a suitable thickness, about 4-6 mm in thickness. The soft silicone jell pad or layer further comprises a plurality of silicone jell beads of suitable dimensions, for example, about 4 mm thick and about 10 mm in length. All beads are inter-connected via soft silicone jell material threads of suitable thickness during the molding process of silicone jell beads. The silicone jell beads reside at about equal distances throughout the matrix of the soft silicone jell pad. There is ample of breathing space (openings) for this silicone jell pad.

In another embodiment of the present invention, a method for an exemplary sequence of the mode of action, silicone jell beads are optionally filled with liquid silicone jell and provide static and dynamic pressure, and friction relief to pressure ulcer or chronic wounds. As the silicone jell pad/layer is carved out of silicone jell material which has excellent static and dynamic pressure absorbing (compressive strength), and low surface roughness characteristics (less traction and acts like a lubricated, soft material). It is to be pointed out that the pressure absorbing capability (compressive strength) is adjustable through viscosity control changes during the preparation of the silicone jell solution. The silicone jell beads are elliptical in shape. The elliptical shape is selected to avoid any concentrated load on the pressure ulcer or the pressure ulcer surrounding areas.

In another embodiment of the present invention, a method for an exemplary sequence of the mode of action, wherein the silicone jell pad has at least about 50% open area to facilitate the breathing of the wound. The silicone jell pad is placed above the absorbent pad in the stacking order of the multilayer wound dressing. Placing the jell pad above the absorbent pad yields optimum pressure distribution to and around the pressure ulcer prone areas.

In another embodiment of the present invention, a method for an exemplary sequence of the mode of action, wherein the silicone jell pad is almost flat, because almost flat base of the beads, with maximum contact to other pads, yields an optimum redistribution of pressure. The silicone jell pad design ensures a steady and ample air flow for breathing purposes.

In another embodiment of the present invention, a method for an exemplary sequence of the mode of action, wherein the surface roughness for the soft silicone jell pad is kept relatively low to avoid and/or to reduce the friction effect. The wound contact layer is made from textured material.

In another embodiment of the present invention, a method for an exemplary sequence of the mode of action the other pads comprising the multilayer dressing, for example, protective mask, hyper-absorbent lock away core, hydro cellular foam pad etc. are made from textured materials in order to reduce the friction effects when the patient turns around or changes positions in the bed. It is also important to use bedding which is made from synthetic fabrics to keep the friction factor at a minimal.

In another embodiment of the present invention, the underside and upper side of outer peripheral edges, up to about 5 mm in width of all layers/pads of the multilayer dressing, are coated with a low adhering adhesive, including but not limited to, acrylic, polyurethane, or silicone adhesive. However, unlike prior art, no adhesive is coated/introduced in the matrix of any of the layers. Reason: If the entire surfaces of multi-pads are coated with adhesive, it will block the pores of the pads and impair breathability of the pads, and thus rendering the overall performance of the dressing unacceptable. The low adherent adhesive is gentle on the skin and makes the change overs easier and pain free. It is patient friendly.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE DRAWINGS

Figure 1:
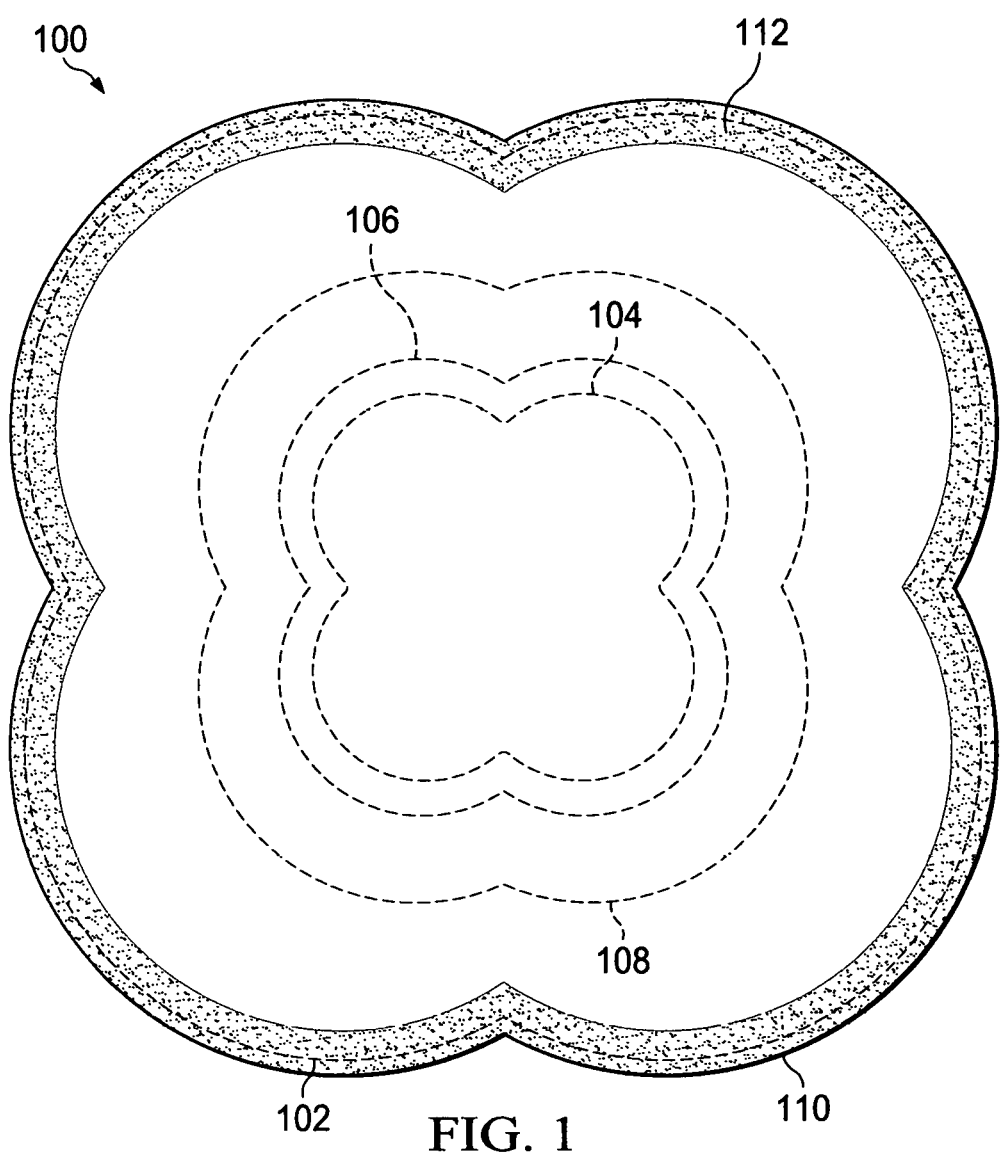
FIG. 1 depicts a comprehensive view of the device, a multilayer dressing which includes all the necessary protective pads in a logical order, in accordance with an embodiment of the present invention.

The present invention is best understood by reference to the detailed figures and description set forth herein.

Embodiments of the present invention are discussed below with reference to the Figures. However, those skilled in the art will readily appreciate that the detailed description given herein with respect to these figures are for explanatory purposes as the invention extends beyond these limited embodiments. For example, it must be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, in another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

The present disclosure's variations and modifications will be apparent to persons skilled in the art. Such variations and modifications may involve equivalent and other features which are already known in the art, and which may be used instead of or in addition to features already described herein.

Features described in the context of separate embodiments may also be provided in combination in a single embodiment. Conversely, various features which are, for brevity, described in the context of a single embodiment, may also be provided separately or in any suitable sub-combination. The Applicants hereby give notice that new Claims may be formulated to such features and/or combinations of such features during the prosecution of the present Application or of any further Application derived therefrom.

References to "one embodiment," "an embodiment," "exemplary embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is well known to those skilled in the art that several careful considerations and compromises typically must be made when designing for the optimal manufacture of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be further understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

It is specifically emphasized that any teaching or combination of teachings, any novel feature, or any novel combination of features including the novel processing mechanism, or any combination of novel processing mechanisms for the multilayer dressing system and method, in accordance with an embodiment of the present invention, is clearly distinguished from the prior art as cited above. As in the present invention, there are no findings in the prior art that teach, or suggest a system or a method using soft silicone jell pad with silicone jell beads, for preventing or treating pressure ulcers by absorbing and/or transferring the patient's body weight, eventually, to the bedding or any other article on which the patient is situated.

It is further emphasized that the present invention significantly differentiates itself from the prior art, and in particular, U.S. Pat. No. 7,982,087, titled: "wound dressing" teaches a system and method and for preventing or treating a pressure ulcers.

It is further emphasized that the present invention also significantly differentiates itself from the disclosed prior art, U.S. Pat. No. 5,759,570 titled: "Multilayer Wound Dressing" which teaches a system and method for preventing or treating pressure ulcers.

However, prior art U.S. Pat. No. 7,982,087 and U.S. Pat. No. 5,759,570 do not teach or suggest a multilayer dressing for preventing or treating a pressure ulcer by configuring an extra layer of soft silicone jell pad with silicone beads filled with or without silicone jell for adequate pressure distribution, and additionally, minimizes friction related adverse effect to the pressure ulcer or chronic wounds.

To achieve the forgoing and other objectives and in accordance with the purpose of the present invention, a device and process for making a multilayer dressing to be used for preventing or treating pressure ulcers as depicted in the present invention. It is to be further understood that the present invention is not limited to the particular methodology, system, techniques, uses, and applications, described herein, as these may vary. It is also to be understood that the terminology used herein is used for the purpose of describing particular embodiments only, and is not intended to limit the scope of the present invention in any manner or fashion. The present invention is illustrated by way of example, and not by way of limitation, in the figures of the accompanying drawings in which like reference numerals refer to similar elements and in which:

FIG. 1 is an illustration of the integrated view of the device 100 which is a multilayer dressing and is used for preventing and treating pressure ulcers and chronic wounds.

The FIG. 1 comprises a plurality of layers, with various types of materials, stacked in a specific sequential order which is more suitable for preventing and treating pressure ulcers and chronic wounds. For example, a protective lower layer 102(a,b) is a transparent, highly breathable and its material of construction is polyurethane film. Face 102a represents top side of the Layer, and face 102b represents underside of the layer 102(a,b). However, for clarity and conciseness, face 102(a) and 102(b) are not shown on any of the Figures. The layer 102 keeps the dust and germs away from the wound. Since polyurethane film is water repellant, it allows the patient to take a shower without taking off the multilayer dressing, without affecting any other layer in the multilayer dressing 100 including the wound, not shown in FIG. 1. Additionally, polyurethane film is a slippery material and helps well to minimize the effect of friction. The other layers in the multilayer dressing include, but are not limited to, a wound contact layer 104, a super absorbent layer 106, and a soft silicone jell layer 108 which is configured in between the wound contact layer 104 and the super absorbent layer 106. The top protective layer 110 for which the material of construction is polyurethane film as well. The top protective layer 110 overlaps or covers all other layers of this multilayer dressing of the present invention. Both, the lower protective layer 102, and the upper protective layer 110, which is generally, polyurethane film are designed to have a very sufficient breathing capability. Also, the exudate or the discharge from the wound can easily pass through the pores of polyurethane film. A good breathing ability of this layer 102 is essential for the healing of ulcer wound (not shown in FIG. 1).

Referring to FIG. 1 again, only the underside of the lower protective layer 102 at its extreme outer periphery to about 10 mm in width is coated with a transparent low adhering adhesive 112. The low adhering adhesive 112 may include, but not limited to acrylic, polyurethane or some other low adhering adhesive.

The low adhering adhesive 112 coating on the peripheral edges of various layers is about 10 mm in width. Note: The low adhering adhesive 112 coating is not applied to the matrix of any layer, because it may adversely affect the permeability or breathing ability of the layers by closing the pores in the matrix of the layers of the dressing.

Referring again to FIG. 1, a super absorbent layer 104 is configured/placed between lower transparent layer 102, and the wound contact layer 104. The super absorbent layer 106 is constructed from the foam such as the polyurethane foam. The top polyurethane layer 110 covers all other layers up to their outer peripheral edges. The silicone layer 108 is placed above the super absorbent layer 106 of the multilayer dressing as shown in FIG. 1.

Figure 2:
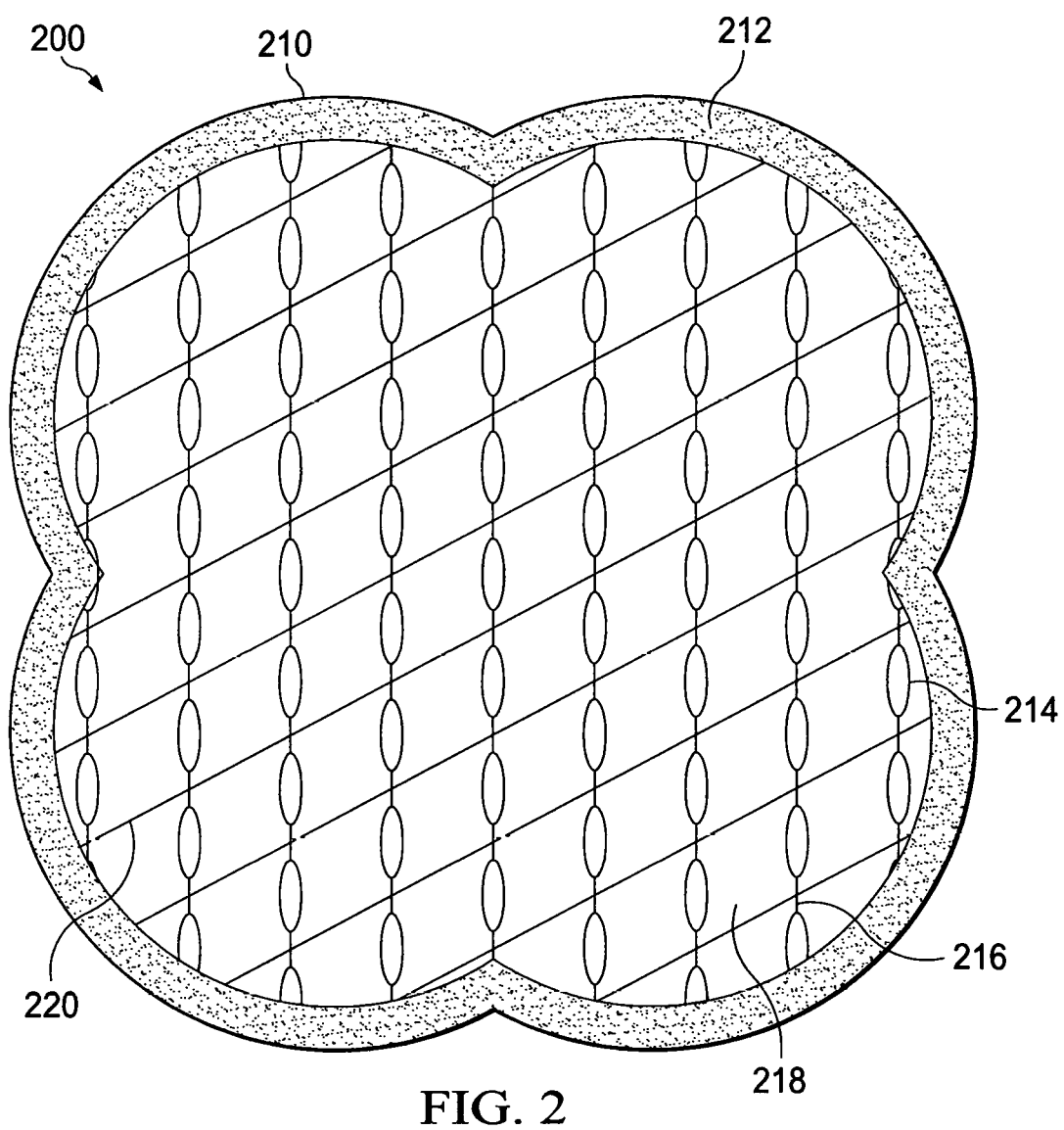
FIG. 2 is an illustration of an exemplary schematic showing a detailed view of the protective silicone jell layer of the multilayer dressing, in accordance with an embodiment of the present invention.

FIG. 2 is an illustration of the layer 108 which depicts an view of the silicone layer 108 as shown in FIG. 1. The soft silicone jell pad or layer 108 is represented with the layer 200 which includes silicone beads 214. The silicone beads 214 are populated throughout the matrix of the layer 200. The beads 214 may be filled with silicone jell, air, Nitrogen, a noble gas or with any other suitable material for adequate pressure distribution.

Again referring to FIG. 2 wherein 210 is upper protective layer, and 212 is an adhesive coating which is about 10 mm wide at the outer periphery. This being the last coating, it is coated only on the underside of the protective layer 102 in FIG. 1. The beads are being represented by 214. The beads are about 10 mm in length and about 5 mm in thickness. All beads are interconnected with each other with the silicone threads such as 216 and 220. The threads 216 and 220 of suitable thickness are part of the construction process of the layer 108 in FIG. 1. The layer 200 offers well designed breathing spaces such as 218. The beads 214 are uniformly distributed symmetrically and at equal distances from each other. Silicone jell filled beads 214 accommodate and uniformly distributes the pressure exerted by the patient's body over an extended area of the silicone layer 108 as shown in FIG. 1.

Figure 3:
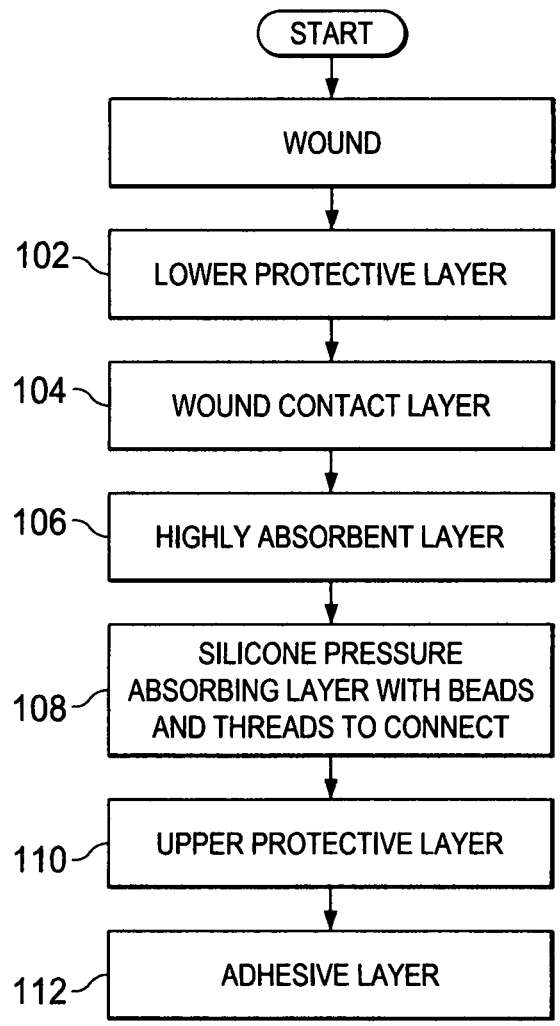
FIG. 3 is an illustration of an exemplary schematic showing a process flow diagram of the multilayer dressing, in accordance with an embodiment of the present invention.

FIG. 3 is an illustration of the process flow diagram for the multilayer wound dressing. The process describes the sequential stacking order of the multilayer wound dressing. The process flow diagram is self-explanatory.

Having fully described at least one embodiment of the present invention, other equivalent or alternative methods of providing a method and device for the multilayer dressing will be apparent to those skilled in the art. The invention has been described above by way of illustration, and the specific embodiments disclosed are not intended to limit the invention to particular forms disclosed. For example, the particular implementation of the method and system may vary depending upon a particular type of application for which it is to be used. However, similar alternatives may be used, for example; refining or improving the present invention is contemplated as within the scope of the present invention. The invention is thus, to cover all modifications, equivalents, and alternatives falling within the spirit and scope of the following claims.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Claim elements and steps herein may have been numbered and/or lettered solely as an aid in readability and understanding. Any such numbering and lettering in itself is not intended to and should not be taken to indicate the ordering of elements and/or steps in the claims.

We claim:

1. A multilayer wound dressing, wherein the multilayer dressing is configured to operate as a passive dressing when applied to a wound, wherein the dressing comprises:
   a lower transparent protective layer;
   a wound contact layer;
   an absorbent layer;
   a silicone jell layer comprising silicone beads; and
   an upper transparent protective layer;
   wherein outer edges of the wound contact layer, the absorbent layer and the silicone jell layer are bounded with a low adhering adhesive.

2. The multilayer wound dressing of claim 1, wherein the lower protective layer and the upper protective layers are made from self-adhering polyurethane film, and wherein the wound contact layer, the absorbent layer, silicone jell layer with silicone beads and the protective layers are breathable.

3. The multilayer wound dressing of claim 1, wherein the low adhering adhesive coats an outer margin of about 10 mm in width of the lower protective film, the upper protective film, the wound contact layer, the absorbent layer, and the silicone jell layer, and wherein the low adhering adhesive includes one of acrylic, polyurethane or silicone adhesive.

4. The multilayer wound dressing of claim 1, wherein the absorbent layer is placed over the wound contact layer, and wherein the absorbent layer is made from hydro-cellular foam.

5. The multilayer wound dressing of claim 1, wherein the silicone jell layer comprises a plurality of the silicone jell beads, and wherein the silicone jell beads are hollow and filled with air, noble gas, or low density silicone jell.

6. The multilayer wound dressing of claim 1, wherein the silicone beads are flexible and capable of absorbing and redistributing tensine fores, compressive forces, or shear loading from a chronic wound to the silicone jell layer.

\* \* \* \* \*